(12) United States Patent
Bae et al.

(10) Patent No.: US 8,846,380 B2
(45) Date of Patent: Sep. 30, 2014

(54) REACTION CASSETTE FOR MEASURING THE CONCENTRATION OF GLYCATED HEMOGLOBIN AND MEASURING METHOD THEREOF

(75) Inventors: Byeong-woo Bae, Anyang-si (KR); Sung-dong Lee, Anyang-si (KR); Min-sun Kim, Seoul (KR); Jae-hyun Yoo, Seoul (KR); Hyoung-soo Kim, Suwon-si (KR); Ki-won Lee, Pocheon-si (KR); Ju-pyo Hong, Seoul (KR)

(73) Assignee: Infopia Co., Ltd., Anyang-si (KR)

( * ) Notice: Subject to any disclaimer, the term of this patent is extended or adjusted under 35 U.S.C. 154(b) by 1154 days.

(21) Appl. No.: 12/025,443

(22) Filed: Feb. 4, 2008

(65) Prior Publication Data
US 2009/0093012 A1 Apr. 9, 2009

(30) Foreign Application Priority Data
Oct. 8, 2007 (KR) .................. 10-2007-0101116

(51) Int. Cl.
C12M 1/34 (2006.01)
G01N 33/72 (2006.01)
G01N 33/543 (2006.01)
B01L 3/00 (2006.01)

(52) U.S. Cl.
CPC ........ *G01N 33/723* (2013.01); *G01N 33/54306* (2013.01); *B01L 2200/0621* (2013.01); *G01N 33/726* (2013.01); *B01L 2400/0457* (2013.01); *B01L 3/502* (2013.01)
USPC .................................. 435/287.1; 435/288.3

(58) Field of Classification Search
USPC ........................................ 435/287.1, 288.3
See application file for complete search history.

(56) References Cited

U.S. PATENT DOCUMENTS

| | | | |
|---|---|---|---|
| 4,818,850 | A | 4/1989 | Gombrich et al. |
| 5,162,237 | A | 11/1992 | Messenger et al. |
| 5,807,747 | A | 9/1998 | Wallworth et al. |
| 6,162,654 | A | 12/2000 | Kawabe |
| 6,174,728 | B1 | 1/2001 | Ben-David et al. |
| 6,300,142 | B1 | 10/2001 | Andrewes et al. |
| 6,562,581 | B2 | 5/2003 | Law et al. |
| 6,677,158 | B2 * | 1/2004 | Hud et al. .................. 436/67 |

FOREIGN PATENT DOCUMENTS

| | | |
|---|---|---|
| EP | 0339277 | 3/1989 |
| EP | 0616216 | 9/1994 |
| JP | 02022560 | 1/1990 |
| JP | 03046566 | 2/1991 |
| JP | 03186746 | 8/1991 |
| JP | 07005178 | 1/1995 |
| JP | 07175900 | 7/1995 |
| JP | 2001524681 | 4/2001 |
| JP | 2006105638 | 4/2006 |
| JP | 2006149215 | 6/2006 |
| JP | 2007198949 | 8/2007 |
| KR | 10-1991-0003383 | 2/1991 |
| KR | 10-2004-0018893 | 3/2004 |
| KR | 10-2006-0009665 | 2/2006 |
| KR | 100662021 | 12/2006 |

OTHER PUBLICATIONS

Muser et al. "Inter-laboratory evaluvation of the COBAS INTEGRA 400 analytical system", Clin Chem Lab Med, 2001, 39(6):539-559.*
European Search Report for application No. 08001622.3 dated Jul. 17, 2009.

* cited by examiner

*Primary Examiner* — Bin Shen
(74) *Attorney, Agent, or Firm* — Westerman, Hattori, Daniels & Adrian, LLP

(57) ABSTRACT

A reaction cassette for a glycated hemoglobin meter and a measuring method thereof are provided. The reaction cassette for the glycated hemoglobin meter includes: a first zone receiving a first reagent and a blood sample; a second zone receiving a second reagent; a reaction zone in which the blood sample reacts with the first reagent, or through which the second reagent passes to react with a first blood sample mixture obtained by reacting the blood sample with the first reagent; and a measurement zone measuring an amount of total hemoglobin in the first blood sample mixture, or measuring an amount of glycated hemoglobin in a second blood sample mixture obtained by reacting the first blood sample mixture with the second reagent, wherein the blood sample, the first reagent, and the second reagent move between the reaction zone and the measurement zone according to a rotation angle of the reaction cassette when the reaction cassette is rotated. Therefore, since the reaction cassette rotates automatically, it is possible to measure the amount of glycated hemoglobin in a blood sample through simple manipulation and reduce a manufacturing time. Furthermore, since reagents are supplied to the reaction cassette from a separate reagent pack, it is possible to resolve storage and distribution problems of the reaction cassette, which occur when reagents are stored in the reaction cassette.

24 Claims, 8 Drawing Sheets

REACTION CASSETTE FOR MEASURING THE CONCENTRATION OF GLYCATED HEMOGLOBIN AND MEASURING METHOD THEREOF

CROSS REFERENCE TO RELATED APPLICATIONS

This application claims priority from Korean Patent Application No. 10-2007-0101116, filed on Oct. 8, 2007, the disclosure of which is incorporated herein in its entirety by reference.

BACKGROUND OF THE INVENTION

1. Field of the Invention

The present invention relates to an apparatus and method for diagnosing diabetes, and more particularly, to an apparatus and method for measuring the concentration of glycated hemoglobin in blood.

2. Description of the Related Art

Medical diagnosis, medical treatment through medicine, and concentration measurement of analytes of anesthetics or harmful chemical materials are useful in medical or environmental technical fields. Concentration measurement of biological samples used for medical diagnosis and treatment is becoming the center of attentions with increase of human desires that want to get freedom from various diseases. Particularly, measurement of glycated hemoglobin in blood is useful to diagnose diabetes because it can expect the average value of blood sugar for a relative long term through one-time measurement, and accordingly, interest on measurement of glycated hemoglobin in blood is also increasing.

Glycated hemoglobin exists in red blood cells in blood. When the concentration of blood sugar (glucose) in blood is high, a part of the glucose in the blood is combined with hemoglobin. The hemoglobin combined with the glucose is called glycated hemoglobin, or HbA1c. Blood sugar levels can be determined by measuring the concentration of glycated hemoglobin in the blood. The measurement of glycated hemoglobin in the blood can be conducted regardless of mealtime.

However, in the case of conventional glycated hemoglobin measurement which has been carried out in a clinical pathology laboratory of a hospital, sample preparation is required, the size of measuring equipment is large, and reagents and consumables are expensive.

Meanwhile, U.S. Pat. No. 6,300,142 discloses an apparatus for reacting a test sample with a reactant in a first injection port and sequentially reacting the lest sample with a second reactant in a second injection port to measure an analyte existing in the test sample. In the U.S. patent, the measurement of the analyte is conducted periodically and sequentially, and a user has to intervene in the measuring process in such a manner that he or she injects the test sample sequentially to react the test sample with other materials. Also, since beads combined with glycated hemoglobin have to be filtered, the measuring process requires a long time.

That is, since the conventional measuring process requires the user's direct intervention in various processing steps, the user may feel inconvenient. Also, the user's direct intervention makes the measuring process more complicated, which further increases the measuring time.

SUMMARY OF THE INVENTION

The present invention provides a reaction cassette for automatically measuring the concentration of glycated hemoglobin in blood, and a measuring method thereof.

The present invention also provides a reaction cassette which can solve its storage and distribution problems because reagents are supplied thereto from a separate reagent pack.

Additional aspects of the invention will be set forth in the description which follows, and in part will be apparent from the description, or may be learned by practice of the invention.

In order to achieve the above objects, the present invention discloses a reaction cassette which can measure the concentration of glycated hemoglobin in a blood sample in a short time, and a measurement method thereof.

According to an aspect of the present invention, there is provided a reaction cassette for a glycated hemoglobin meter, the reaction cassette including: a first zone receiving a first reagent and a blood sample; a second zone receiving a second reagent; a reaction zone in which the blood sample reacts with the first reagent, or through which the second reagent passes to react with a first blood sample mixture obtained by reacting the blood sample with the first reagent; and a measurement zone measuring an amount of total hemoglobin in the first blood sample mixture, or measuring an amount of glycated hemoglobin in a second blood sample mixture obtained by reacting the first blood sample mixture with the second reagent, wherein the blood sample, the first reagent, and the second reagent move between the reaction zone and the measurement zone according to a rotation angle of the reaction cassette when the reaction cassette is rotated.

According to another aspect of the present invention, there is provided a method for measuring an amount of glycated hemoglobin in a blood sample using a reaction cassette for a glycated hemoglobin meter, the reaction cassette including: a first zone receiving a first reagent and a blood sample; a second zone receiving a second reagent; a reaction zone in which the blood sample reacts with the first reagent, or through which the second reagent passes to react with a first blood sample mixture obtained by reacting the blood sample with the first reagent; and a measurement zone measuring an amount of total hemoglobin in the first blood sample mixture, or measuring an amount of glycated hemoglobin in a second blood sample mixture obtained by reacting the first blood sample mixture with the second reagent, wherein the blood sample, the first reagent, and the second reagent move between the reaction zone and the measurement zone according to a rotation angle of the reaction cassette when the reaction cassette is rotated, the method including: recognizing information for the reaction cassette; determining whether the blood sample, the first reagent, and the second reagent are discharged into the reaction cassette; reacting the blood sample with the first reagent; rotating the reaction cassette to measure the amount of total hemoglobin in the first blood sample mixture; rotating the reaction cassette to measure the amount of glycated hemoglobin in the second blood sample mixture; and calculating a ratio of the amount of glycated hemoglobin in the second blood sample mixture with respect to the amount of total hemoglobin in the first blood sample mixture, on the basis of the amount of total hemoglobin and the amount of glycated hemoglobin.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the aspects of the invention.

DETAILED DESCRIPTION OF EXEMPLARY EMBODIMENTS

Figure 1:
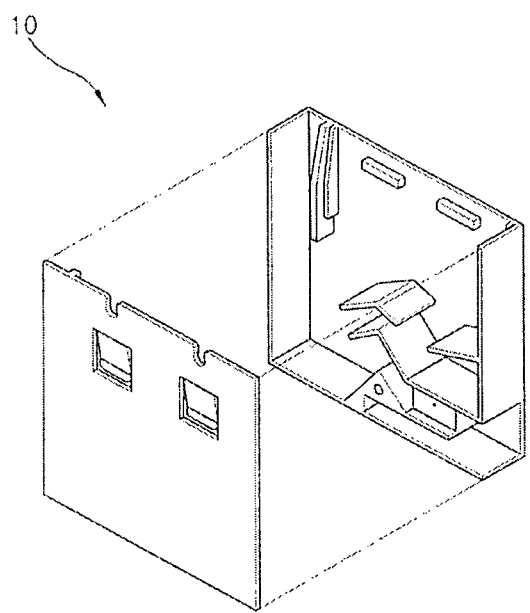
FIG. 1 is a perspective view of a reaction cassette according to an embodiment of the present invention.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

FIG. 1 is a perspective view of a reaction cassette 10 according to an embodiment of the present invention.

The reaction cassette 10 is used to measure the concentration of glycated hemoglobin (HbA1c) in a blood sample. When the concentration of glycated hemoglobin (HbA1c) in a blood sample is measured, the reaction cassette 10 enters a glycated hemoglobin meter 30 (see FIG. 4) and is rotated clockwise or counterclockwise with respect to a predetermined axis.

When the reaction cassette 10 is rotated by the glycated hemoglobin meter 30, the blood sample and reagents are mixed and react with each other in the respective zones of the reaction cassette 10, and thus a user needs not to add the reagents to the blood sample at regular intervals, which reduces a measuring time. Here, the term "reaction" is meaning including a chemical reaction, agitating, washing, etc.

The construction of the reaction cassette 10 will be described in detail with reference to FIG. 3, later.

Figure 2:
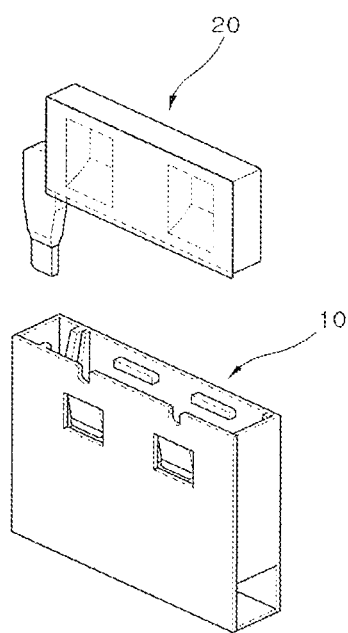
FIG. 2 illustrates an external appearance of a reagent pack according to an embodiment of the present invention.

FIG. 2 illustrates an external appearance of a reagent pack 20 according to an embodiment of the present invention.

In order to measure the concentration of glycated hemoglobin in the blood sample, at least one reagent which reacts with the blood sample has to be supplied to the reaction cassette 10. The reagent is supplied from a reagent pack 20 which can be packed and sold.

The reagent pack 20 is inserted into the upper portion of the reaction cassette 20. When the reagent pack 20 is inserted into the upper portion of the reaction cassette 10, at least one reagent stored in the reagent pack 20 is poured into the reagent cassette 10.

Figure 3:
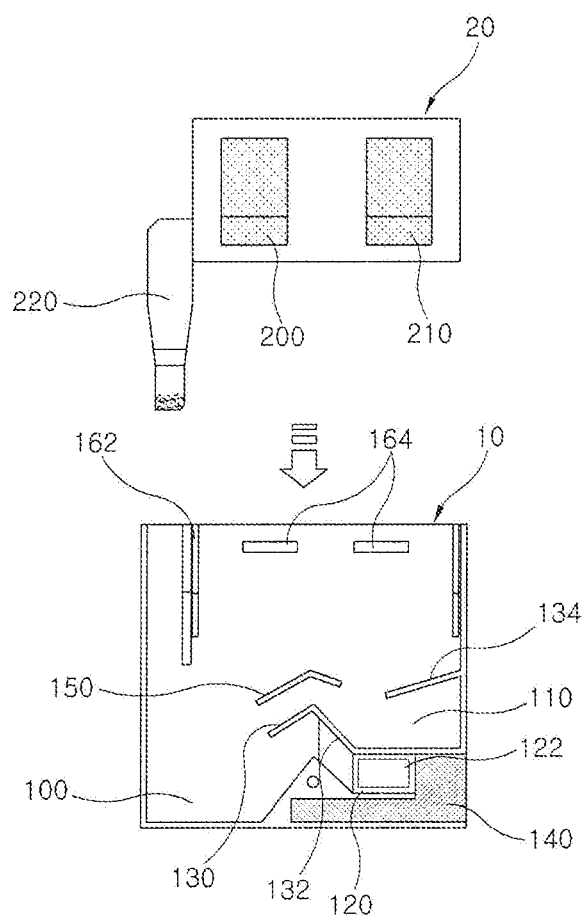
FIG. 3 shows cross-sectional views of the reaction cassette and the reagent pack illustrated respectively in FIGS. 1 and 2.

FIG. 3 shows cross-sectional views of the reaction cassette 10 and the reagent pack 20 illustrated respectively in FIGS. 1 and 2.

The reagent pack 20 includes a first storage holder 200 and a second storage holder 210. The reagent pack 20 can further include a blood sampling tube 220.

The first and second storage holders 200 and 210 each stores at least one reagent. For example, the first storage holder 200 stores a first reagent which reacts with a blood sample. In this case, the amount of glycated hemoglobin in a blood sample mixture obtained when the blood sample reacts with the first reagent is measured. For example, the first reagent includes a hemolysate which hemolyzes the blood sample, and glycated hemoglobin binding material-beads which combine specifically with glycated hemoglobin.

The hemolysate is a buffer solution containing a surface active agent. For example, the hemolysate is N-2-Hydroxyethylpiperazine-N'-2-ethanesulfonic Acid HEPES; pH 8.1. The blood sample hemolyzed by the hemolysate includes non-glycated hemoglobin and glycated hemoglobin.

The glycated hemoglobin binding material is a material which can combine specifically with glycated hemoglobin, for example, the glycated hemoglobin-binding material is one of boronic acid (BA), concanavalin A (Lectin), and antibody. The beads may be polymer polysaccharide support (such as agarose, cellulose, or sepharose), latex beads (such as polystyrene, polymethylmethacrylate, or polyvinyltolune), or glass beads. It is preferable that the diameter of each glycated hemoglobin binding material-bead is set in consideration with a precipitation time of the glycated hemoglobin binding material-bead combined with glycated hemoglobin after reaction, and reactivity with respect to glycated hemoglobin.

Meanwhile, the second storage holder 210 of the reagent pack 20 stores a second reagent. The second reagent may include a washing solution for washing off the blood sample mixture. Most of hemoglobin (Hb) existing in red blood cells of a blood sample is non-glycated hemoglobin (Ao). Only 4.0-14.0% of the non-glycated hemoglobin reacts with glucose, and becomes glycated hemoglobin (HbA1c). Accordingly, the blood sample mixture which has reacted with the glycated hemoglobin binding material-beads of the first reagent includes both non-glycated hemoglobin and glycated hemoglobin. Therefore, in order to measure only the glycated hemoglobin in the blood sample, it is needed to remove the non-glycated hemoglobin from the blood sample. For this reason, the second reagent includes a washing solution for washing off the non-glycated hemoglobin from the blood sample.

Meanwhile, the reagent pack 20 can further include the blood sampling tube 220 for receiving a blood sample to be measured. The blood sampling tube 220 may be a capillary lube because it can suck in a blood sample that is to be measured. Particularly, the inside diameter of the tip of the blood sampling tube 220 is smaller than that of the remaining portion of the blood sampling tube 220 so that the capillary phenomenon is generated.

In summary, the first and second reagents can be simultaneously supplied to the reaction cassette 10 from the reagent pack 20. Accordingly, a user needs not to supply reagents that will react with a blood sample at regular intervals in order to measure the concentration of glycated hemoglobin in the blood sample. For example, it is unnecessary to supply the first reagent to a measurement zone to measure the amount of total hemoglobin in the blood sample, and then supply the second reagent to the measurement zone to measure the amount of glycated hemoglobin in the blood sample.

That is, according to the present invention, since the reaction cassette 10 is automatically rotated to perform reactions such as combining and agitation of reactants, the first and second reagents can be simultaneously supplied to the reaction cassette 10.

Meanwhile, the reagent pack 20 can further include a foil cover and a foil tap. The foil cover is used to seal up the first and second reagents stored in the first and second storage holders 200 and 210 and thus prevent the first and second reagents from leaking out. When the reagent pack 20 is inserted into the reaction cassette 10, the foil tap of the reagent pack 20 is caught by a locking jaw of the reaction cassette 10 and the foil cover of the reagent pack 20 is taken off. Accordingly, when the reagent pack 20 is inserted into the reaction cassette 10, the first and second reagents in the reagent pack 20 are poured into the reaction cassette 10.

Meanwhile, the reaction cassette 10 includes a first zone 100, a second zone 110, a reaction zone, and a measurement zone 120. Also, the reaction cassette 10 can further include a delivery guide unit 130 and a reagent absorption unit 140. The first zone 100 can receive the first reagent and the blood sample, and the second zone 110 can receive the second reagent. As described above with reference to FIG. 2, the first reagent may include a hemolysate and glycated hemoglobin binding material-beads, and the second reagent may include a washing solution.

When the reagent pack 20 is inserted into the reaction cassette 10, the first and second reagents stored in the reagent pack 20 are poured respectively into the first and second zones 100 and 110. The reaction cassette 10 can further include a zone dividing unit 150. The zone dividing unit 150 guides the first and second reagents to the first and second zones 100 and 110, respectively.

In the reaction zone, the blood sample reacts with the first reagent. Here, the term "reaction" is meaning including a chemical reaction, agitating, washing, etc. The reaction zone is physically the same space as the first zone 100. That is, the blood sample reacts with the first reagent in the first zone 100. When the reaction cassette 10 is rotated, the second reagent in the second zone 110 is transferred to the first zone 100. Then, if the reaction cassette 10 is again rotated, the second reagent is transferred to the measurement zone 120, so that the second reagent reacts with the blood sample mixture of the blood sample and the first reagent.

In the measurement zone 120, the amount of total hemoglobin in the blood sample mixture of the blood sample and the first reagent is measured by a predetermined method, for example, by an optical reflectometry technique. For example, the amount of total hemoglobin in the blood sample mixture is measured by utilizing the characteristic that hemoglobin specifically absorbs an optical signal of a specific frequency. That is, the concentration of hemoglobin can be measured by relatively measuring the strengths of light or the densities of colors, using the characteristic of hemoglobin.

Also, the measurement zone 120 can further include an optical window 122 from which light received through an external optical sensor is reflected, in order to measure optical reflectance. The external optical sensor is installed in the glycated hemoglobin meter 30 which the reaction cassette 10 enters.

Meanwhile, the reagent absorption unit 140 absorbs the blood sample mixture from which glycated hemoglobin has been measured, thus preventing the blood sample mixture from leaking out. In order to measure the amount of glycated hemoglobin in the blood sample, the reagent absorption unit 140 can absorb non-glycated hemoglobin which exists in the measurement zone 120 and the remaining materials except for glycated hemoglobin binding material-beads combined with glycated hemoglobin. The reagent absorption unit 140 may be disposed below the measurement zone 120. The reagent absorption unit 140 may be an absorptive pad.

The measurement cassette 10 includes a first partition wall 132 and a second partition wall 134 around the measurement zone 120.

The first partition wall 132 separates the second zone 110 from the measurement zone 120, and also prevents the second reagent in the second zone 110 from moving to the first zone 100 within a specific rotation angle range. Due to the second partition wall 134, the second reagent (washing solution) in the second zone 110 does not move to any other zone within a specific rotation angle range, for example, within a rotation angle range of −15 through 70 degrees.

The reaction cassette 10 can further include a partition wall (not shown), an insertion guide unit 162, and a reagent pack locking jaw 164.

The partition wall (not shown) separates the first reagent from the second reagent so that the first reagent, the blood sample, and the second reagent are not mixed with each other when the reagent pack 20 is inserted into the reaction cassette 10. The zone dividing unit 150 separates the first reagent from the second reagent and guides the movement of the first and second reagents when the first reagent and the blood sample are discharged into the first zone 100 and the second reagent is discharged into the second zone 110. The insertion guide unit 162 guides the reagent pack 20 to its exact position when the reagent pack 20 is inserted into the reaction cassette 10. When the reagent pack 20 is inserted into the reaction cassette 10, the foil tap of the reagent pack 20 is caught and uncovered by the reagent pack locking jaw 164, and thus, the first and second reagents are poured into the first and second zones 100 and 110, respectively.

Figure 4:
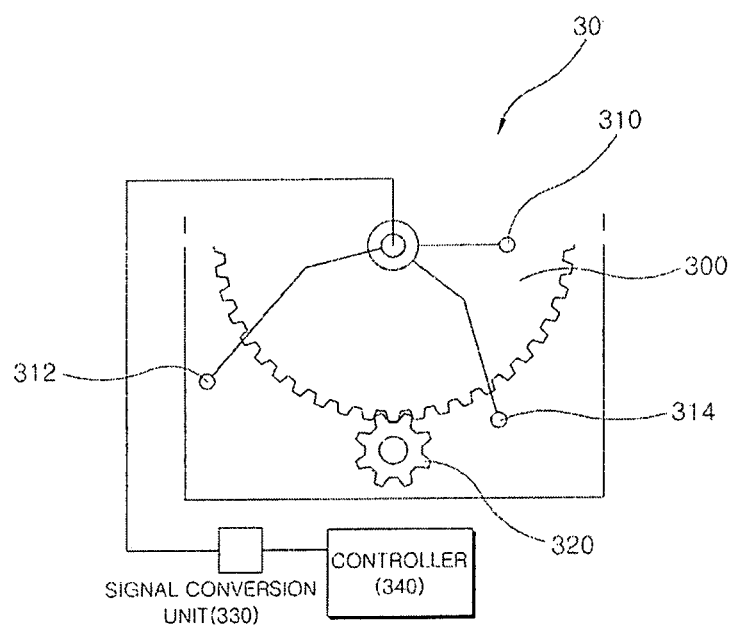
FIG. 4 is a schematic view showing a glycated hemoglobin meter according to an embodiment of the present invention.

FIG. 4 is a schematic view showing the glycated hemoglobin meter 30 according to an embodiment of the present invention. Referring to FIG. 4, the reaction cassette 10 enters the glycated hemoglobin meter 30, and the glycated hemoglobin meter 30 rotates the reaction cassette 10 clockwise or counterclockwise according to a predetermined rule. The rotation is aimed at automatically agitating a blood sample with a first or second reagent or moving the blood sample mixture to a different zone in the reaction cassette 10 in order to measure the concentration of glycated hemoglobin in the blood sample.

Also, the glycated hemoglobin meter 30 measures the concentration of glycated hemoglobin using the optical reflectometry technique. For example, a characteristic that hemoglobin specifically absorbs an optical signal of a specific frequency is utilized. In the current embodiment, the glycated hemoglobin meter 30 measures the amount of glycated hemoglobin using a light-emitting unit such as a photo diode and a light-receiving device.

Referring to FIG. 4, the glycated hemoglobin meter 30 includes a cassette accommodation portion 300, a first cassette check sensor 310, a second cassette check sensor 312, a measurement sensor 314, a driving unit 320, a signal conversion unit 330, and a controller 340.

The cassette accommodation portion 300 has a space into which the reaction cassette 10 will be inserted. It is preferable that the cassette accommodation portion 300 has a sufficient space so that the reaction cassette 10 can be rotated clockwise or counterclockwise without any interruption therein.

Meanwhile, the glycated hemoglobin meter 30 includes sensors, such as the first cassette check sensor 310, the second cassette check sensor 312, and the measurement sensor 314. The first cassette check sensor 310 reads a barcode attached on the outer surface of the reaction cassette 10. The second cassette check sensor 312 determines whether solutions including reagents such as the first reagent and the second reagent are properly poured into the first and second zones 100 and 110 of the reaction cassette 10. The second cassette check sensor 312 detects the existence or absence of reagents using an absorption photometry method. According to the absorption photometry method, the second cassette check sensor 312 passes an optical signal through the reaction cassette 10 using a light-emitting unit, receives the optical signal through a light-receiving unit, and converts the optical signal into an electrical signal, thereby determining whether the first and second reagents are properly stored into the first and second zones 100 and 110.

The measurement sensor 314 measures the amount of total hemoglobin and the amount of glycated hemoglobin which are contained in the measurement zone 120 of the reaction cassette 10. That is, by outputting a light-emitting control signal to the light-emitting unit and converting an optical signal received from the light-receiving unit into an electrical signal, the amount of hemoglobin contained in the reaction cassette 10 can be measured.

Meanwhile, the driver 320 applies power to the reaction cassette 10. For example, the driver 320 may be a motor. The reaction cassette 10 rotates according to a predetermined rule by the power. The signal conversion unit 330 may be an Analog-to-Digital (A/D) converter.

The controller 340 may be a microprocessor into which a ROM, a RAM, and peripheral devices are integrated. The controller 340 can identify the reaction cassette 10, determine whether reagent solutions are injected into the reaction cassette 10, or measure the amount of glycated hemoglobin in a blood sample.

That is, the controller 340 identifies the type and code information of the reaction cassette 10 on the basis of information obtained by converting a barcode image acquired from the first cassette check sensor 310 into a digital signal through the signal conversion unit 330. Also, the controller 340 outputs a light-emitting control signal to the light-emitting unit, and converts an optical signal received from the light-receiving device into an electrical signal through the A/D conversion unit, thereby determining whether the first and second reagents are properly poured into the reaction cassette 10. In this manner, it is possible to measure the amount of glycated hemoglobin included in the measurement zone 120 of the reaction cassette 10 can be measured.

Hereinafter, a method of measuring the amount of glycated hemoglobin in a blood sample using the reaction cassette 10 of the glycated hemoglobin meter 30 will be described in detail with reference to FIGS. 3, 4, 5 and 6A-6D.

Figure 5:
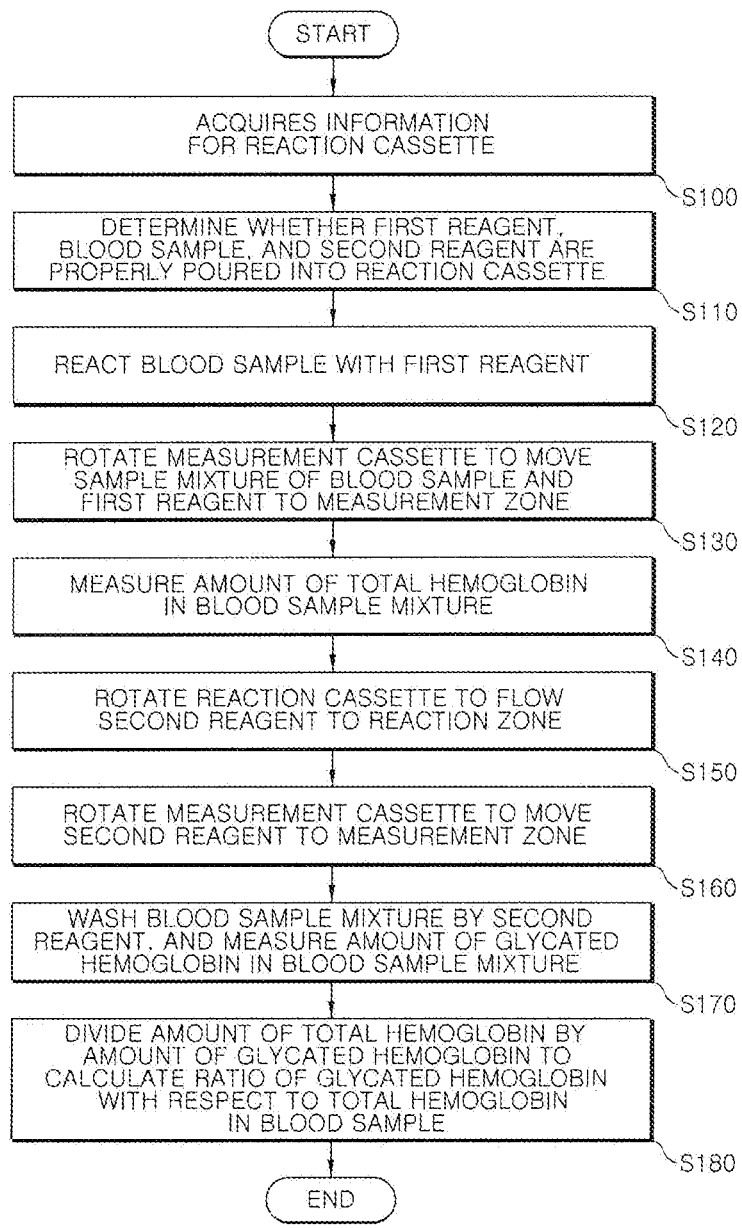
FIG. 5 is a flowchart of a glycated hemoglobin measuring method according to an embodiment of the present invention, which is performed by the reaction cassette illustrated in FIG. 1.

FIG. 5 is a flowchart of a glycated hemoglobin measuring method according to an embodiment of the present invention, which is performed using the reaction cassette 10 illustrated in FIG. 1.

Referring to FIGS. 3, 4, and 5, the glycated hemoglobin meter 30 receives the reaction cassette 10, and acquires information for the reaction cassette 10 (operation S100). At this time, the information for the reaction cassette 10 can be acquired by the first cassette check sensor 310 of the glycated hemoglobin meter 30.

Successively, it is determined whether a first reagent, a blood sample, and a second reagent are properly poured into the reaction cassette 10 (operation S110). The determination is carried out by the second cassette check sensor 312.

Here, the first and second reagents can be supplied from the reagent pack 20 to the reaction cassette 10. When the first and second reagents are supplied to the reaction cassette 10 by inserting the reagent pack 20 into the reaction cassette 10, the first reagent and the second reagent are stored respectively in different zones of the reaction cassette 10. The reason is because the amount of total hemoglobin and the amount of glycated hemoglobin in a blood sample need to be measured respectively according to the respective purposes of the first and second reagents. Accordingly, it is possible to resolve storage and distribution problems of the reaction cassette 10 which may occur when reagents are stored in the reaction cassette 10. Also, it is possible to reduce the size of the reaction cassette 10.

Also, a blood sample is gathered by the blood sampling tube 220. It is preferable that the tip of the blood sampling tube 220 is completely sunk in the first reagent of the first zone 100 when the reaction cassette 10 is positioned horizontally. Then, the glycated hemoglobin meter 30 reacts the blood sample with the first reagent in the reaction zone, that is, in the first zone (operation S120). At this time, it is preferable to shake the reaction cassette 10 clockwise and counterclockwise to facilitate the reaction of the blood sample with the first reagent. This operation is aimed at hemolyzing the blood sample contained in the blood sampling tube 220 with the first reagent to discharge the blood sample from the blood sampling tube 220, and simultaneously reacting the blood sample specifically with glycated hemoglobin binding material-beads. To sufficiently react the hemolyzed blood sample with the glycated hemoglobin binding material-beads, a predetermined time, for example, about 3 minutes can be consumed.

Successively, the measurement cassette 10 is rotated to move a blood sample mixture of the blood sample and the first reagent in the reaction zone to the measurement zone 120 (operation S130). Then, the amount of total hemoglobin in the blood sample mixture is measured in the measurement zone 120 (operation S140). At this time, the amount of total hemoglobin in the blood sample mixture can be measured by the optical reflectometry technique using an optical sensor.

Then, the reaction cassette 10 is rotated to flow the second reagent o the reaction zone (operation S150). When the reaction cassette 10 rotates, the blood sample mixture in the measurement zone 120 does not move to the reaction zone. The reason is because the non-glycated hemoglobin and the glycated hemoglobin binding material-beads combined with the glycated hemoglobin are in a jelly state.

Then, the measurement cassette 10 is rotated so that the second reagent in the reaction zone moves to the measurement zone 120 (operation S160). Successively, the blood sample mixture is washed by the second reagent, and the amount of glycated hemoglobin in the blood sample mixture is measured (operation S170). By washing the blood sample mixture by the second reagent including a washing solution, non-glycated hemoglobin (Ao) in the blood sample is removed. Also, the amount of glycated hemoglobin is measured by the optical reflectometry technique using the optical sensor, like when the amount of total hemoglobin in the blood sample mixture is measured. Then, by dividing the amount of total hemoglobin by the amount of glycated hemoglobin, a ratio of glycated hemoglobin with respect to total hemoglobin in the blood sample is calculated (operation S180) The ratio of glycated hemoglobin with total hemoglobin in the blood sample is calculated by the following equation.

$$\text{Ratio of Glycated Hemoglobin With Respect To Total Hemoglobin}(\%) = \frac{\text{Glycated Hemoglobin}}{\text{Total Hemoglobin}} \times 100 \qquad (1)$$

FIGS. 6A through 6D are exemplary views where the reaction cassette 10 illustrated in FIG. 1 is rotated to measure the amount of glycated hemoglobin in a blood sample, according to an embodiment of the present invention.

Figure 6A:
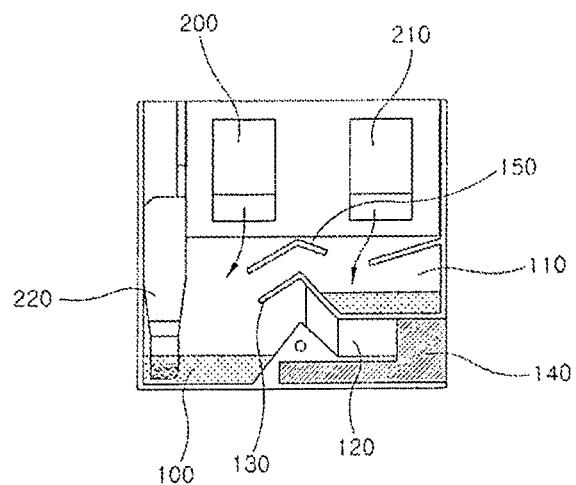
FIGS. 6A through 6D are exemplary views where the reaction cassette illustrated in FIG. 1 is rotated to measure the concentration of glycated hemoglobin in a blood sample, according to an embodiment of the present invention.

Referring to FIGS. 3, 4, and 6A, when a first reagent and a second reagent are supplied from the reagent pack 20 to the reaction cassette 10, the first reagent is supplied to the first zone 100 and the second reagent is supplied to the second zone 110. A blood sample gathered from a human body is supplied to the first zone 100 via the reagent pack 20, and reacts with the first reagent. To facilitate the reaction of the blood sample with the first reagent, it is preferable to shake the glycated hemoglobin meter 30 clockwise and counter-clockwise for a sufficient time, for example, for about 3 minutes.

Figure 6B:
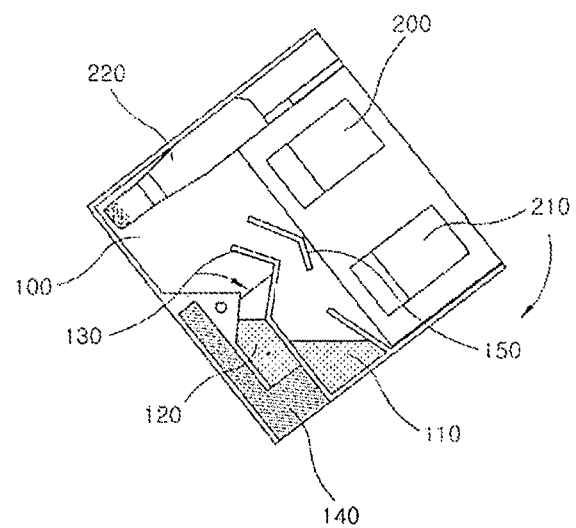

Thereafter, as illustrated in FIG. 6B, the glycated hemoglobin meter 30 rotates the reaction cassette 10 clockwise, so that the blood sample mixture of the blood sample and the first reagent in the reaction zone moves to the measurement zone 120. In the measurement zone 120, the concentrations of non-glycated hemoglobin in the blood sample mixture is measured.

Figure 6C:
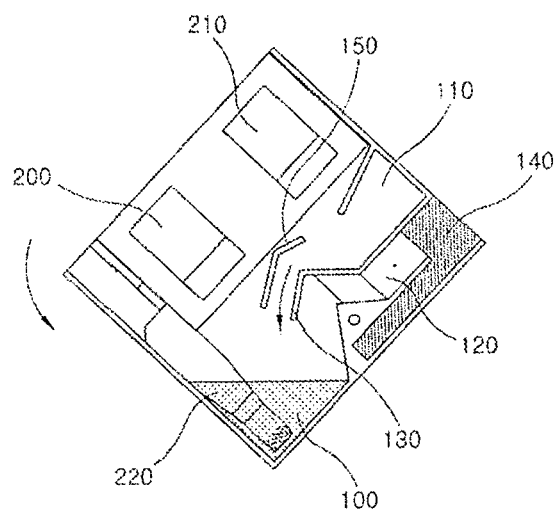
Figure 6D:
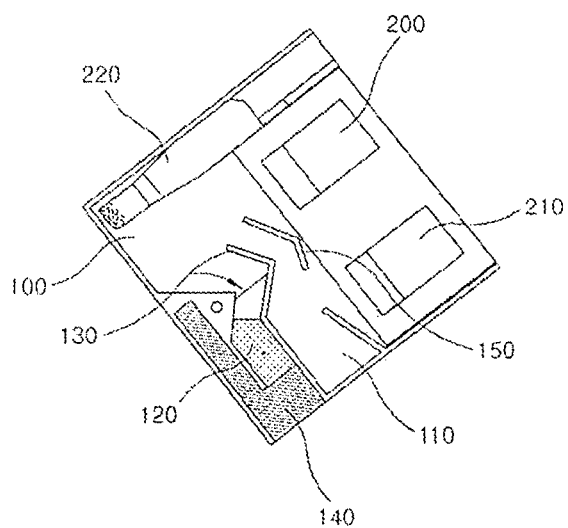

Successively, as illustrated in FIG. 6C, the reaction cassette 10 is rotated counterclockwise, so that the second reagent in the second zone 110 is moved to the reaction zone. Then, as illustrated in FIG. 6D, if the reaction cassette 10 is rotated counterclockwise, the second reagent in the reaction zone is moved to the measurement zone 120 to remove the non-glycated hemoglobin in the blood sample mixture. Then, the amount of glycated hemoglobin in the blood sample mixture is measured.

In summary, as illustrated in FIGS. 6A through 6D, the glycated hemoglobin meter 30 automatically rotates the reaction cassette 10 clockwise or counterclockwise, at least one reagent reacts with glycated hemoglobin or at least one reagent is moved to a different zone in the reaction cassette 10. Accordingly, a user needs not to sequentially supply the first reagent and the second reagent to the reaction cassette 10 at regular intervals and agitate the blood sample with the first reagent. That is, the user can measure an exact concentration of a reactant to be analyzed in a blood sample through simple manipulation.

A different rotation process other than the rotation process described above with reference to FIGS. 6A through 6D can be used. If the respective zones of the reaction cassette 10 are arranged symmetrically unlike the above-described embodiment, it is preferable to rotate the reaction cassette 10 in a reverse direction of the rotation direction mentioned in the above-described embodiment.

Meanwhile, the glycated hemoglobin meter 30 can acquire information for the reaction cassette 10 through a barcode of the reaction cassette 10. The barcode can be used to determine whether the corresponding reaction cassette 10 is available. The barcode may be a fan-shaped barcode 170a illustrated in FIGS. 7 and 8, or a barcode 170b including a graduation pattern and a code pattern aligned in the same direction at a side of the reaction cassette 10.

Hereinafter, various barcode shapes that can be attached on the reaction cassette 10 will be described in detail with reference to FIGS. 7 and 8.

Figure 7:
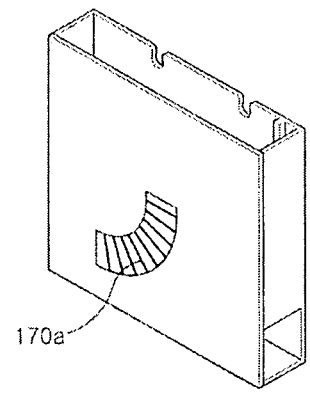
FIG. 7 illustrates a fan-shaped barcode which is used for the reaction cassette illustrated in FIG. 1, according to an embodiment of the present invention.

FIG. 7 illustrates a fan-shaped barcode 170a attached on the reaction cassette 10 illustrated in FIG. 1, according to an embodiment of the present invention.

Referring to FIG. 7, the barcode 170a includes a graduation pattern where lines are drawn at regular intervals in a fan shape. The barcode 170a is disposed on the rear side of the reaction cassette 10. Black bars of the barcode 170a have a low optical reflectance, but white bars of the barcode 170a have a high optical reflectance. Therefore, the glycated hemoglobin meter 30 receives light reflected by the barcode 170a, and converts the light into an electronic signal corresponding to 0 or 1 bit, thereby reading the barcode 170a. That is, the glycated hemoglobin meter 30 acquires information for the reaction cassette 10 by reading the barcode 170a of the reaction cassette 10.

Figure 8:
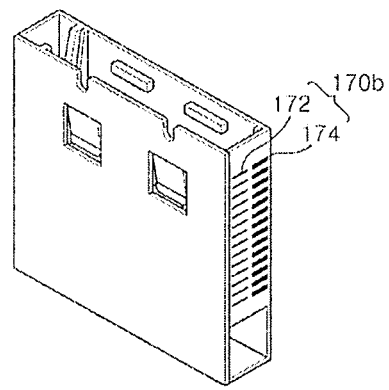
FIG. 8 illustrates a barcode including a graduation pattern and a code pattern, which is used for the reaction cassette illustrated in FIG. 1, according to another embodiment of the present invention.

FIG. 8 illustrates a barcode 170b including a graduation pattern 172 and a code pattern 174 of the reaction cassette 10 illustrated in FIG. 1, according to another embodiment of the present invention.

Referring to FIG. 8, the graduation pattern 172 is a pattern where graduations are drawn at regular intervals and the code pattern 174 is a normal barcode pattern. The graduation pattern 172 and the code pattern 174 are arranged side by side in the same direction at a side of the reaction cassette 10. The reactor cassette 10 is inserted into the glycated hemoglobin meter 30 at an irregular speed. If a barcode is read in synchronization with a sample clock signal, it is difficult to correctly read the barcode because barcode data changes depending on a read speed. In order to resolve the problem, a method of automatically inserting the reaction cassette 10 at a regular speed into the glycated hemoglobin meter 30 using a motor has been proposed. However, the method makes the structure of the glycated hemoglobin meter 30 complicated and increases manufacturing costs thereof.

Accordingly, the glycated hemoglobin meter 30 includes two optical sensors: one is used to read the graduation pattern 172 and the other is used to read the code pattern 174. Since the graduation pattern 172 has more narrow bar intervals than those of the code pattern 174, a speed at which the reaction cassette 10 is inserted into the glycated hemoglobin meter 30 can be measured using the graduation pattern 172.

Accordingly, if the code pattern 174 is read for a predetermined number of graduations, the code pattern 174 can be exactly read regardless of a speed at which the reaction cassette 10 is inserted into the glycated hemoglobin meter 30.

For example, whenever one (hereinafter, referred to as a first optical sensor) of the two optical sensors detects five graduations, the other (hereinafter, referred to as a second optical sensor) of the two optical sensors reads the code pattern 174. Accordingly, the second optical sensor can acquire barcode data at regular intervals in a length direction of the code pattern 174, As described above, according to the present invention, by moving a blood sample to the respective zones of the reaction cassette 10 according to a rotation angle of the reaction cassette 10 and sequentially reacting the blood sample with reagents, the amount of glycated hemoglobin in the blood sample can be automatically measured.

Accordingly, it is possible to reduce a time consumed to measure the concentration of glycated hemoglobin in a blood sample. Since a blood sample reacts with reagents or moves to different zones of the reaction cassette 10 by automatically rotating the reaction cassette 10, a user's manipulation of supplying the reagents to the blood sample is not needed. Accordingly, it is possible to measure the concentration of glycated hemoglobin in a blood sample in a short time through simple manipulation at home or office.

Also, since the reaction cassette according to the present invention receives reagents to react with a blood sample from a separate reagent pack, storage and distribution problems of the reaction cassette can be resolved which may occur when reagents are stored in the reaction cassette. Additionally, it is possible to reduce the size of the reaction cassette. Furthermore, a user needs not to sequentially supply a plurality of reagents to react with a blood sample to the reaction cassette at regular intervals in order to measure the concentration of glycated hemoglobin in the blood sample.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

What is claimed is:

1. A reaction cassette for a glycated hemoglobin meter, the reaction cassette comprising:
   a first zone for receiving a reagent which selectively reacts with glycated hemoglobin and a blood sample;
   a second zone for receiving a washing solution;
   a measurement zone for measuring an amount of total hemoglobin in a blood sample mixture which is a mixture of the reagent and the blood sample, and measuring an amount of glycated hemoglobin in the blood sample mixture from which non-glycinated hemoglobin is removed; and
   a delivery guide unit configured to guide the blood sample mixture to move from the first zone to the measurement zone, without passing through the second zone, according to rotation angles of the reaction cassette,
   wherein the non-glycinated hemoglobin is physically removed from the blood sample mixture by washing the blood sample mixture with the washing solution,
   wherein the reaction cassette is configured such that the blood sample mixture is moved from the first zone to the measurement zone, without passing through the second zone, by gravity when the reaction cassette is rotated in a first direction, and
   wherein the reaction cassette is configured such that the washing solution is moved from the second zone to the first zone by gravity when the reaction cassette is rotated in a second direction.

2. The reaction cassette of claim 1, wherein the reaction cassette is configured such that a reagent pack storing the reagent and the washing solution is insertable into the reaction cassette, the reagent pack discharging the reagent and the washing solution into the first zone and the second zone respectively when the reagent pack is inserted into the reaction cassette.

3. The reaction cassette of claim 2, further comprising a locking jaw by which a foil tap of the reagent pack is caught and uncovered when the reagent pack is inserted into the reaction cassette, thereby discharging the reagent and the washing solution into the first zone and the second zone respectively when the reagent pack is inserted into the reaction cassette.

4. The reaction cassette of claim 1, further comprising an optical window from which light received from an external optical sensor is reflected.

5. The reaction cassette of claim 1, further comprising:
   a first partition wall,
   wherein the first partition wall is configured to prevent the washing solution from moving from the second zone to the first zone when the reagent and the washing solution are discharged from a reagent pack into the first zone and the second zone,
   wherein the combination of the delivery guide unit and the first partition wall is configured to guide the blood sample mixture so as to move from the first zone to the measurement zone, without passing through the second zone, according to the rotation of the cassette in the first direction, and
   wherein the combination of the delivery guide unit and the first partition wall is configured to guide the washing solution so as to move from the second zone to the first zone to according to the rotation of the cassette in the second direction.

6. The reaction cassette of claim 5, wherein the washing solution in the second zone does not move out of the second zone when the reaction cassette is rotated to any angle within a range of −15 to 70 degrees.

7. The reaction cassette of claim 1, further comprising an absorption unit for absorbing the non-glycated hemoglobin removed from the blood sample mixture.

8. The reaction cassette of claim 7, wherein the reagent absorption unit is an absorptive pad.

9. The reaction cassette of claim 1, further comprising a dividing unit for separating the reagent and the washing solution from each other when the reagent and the washing solution are discharged into the reaction cassette.

10. The reaction cassette of claim 1, further comprising a fan-shaped barcode to which information for the reaction cassette is coded.

11. The reaction cassette of claim 1, further comprising a barcode including a graduation pattern and a code pattern which are aligned in the same direction at a side of the reaction cassette.

12. The reaction cassette of claim 1, wherein the reagent includes a hemolysate and glycated hemoglobin binding material-beads which selectively react with glycated hemoglobin, and the beads are agarose beads, sepharose beads, latex beads, or glass beads.

13. The reaction cassette of claim 12, wherein the glycated hemoglobin binding material of the glycated hemoglobin binding material-beads is boronic acid (BA).

14. The reaction cassette of claim 1, wherein the blood sample mixture is formed by agitating the blood sample and the reagent together to make a chemical reaction.

15. The reaction cassette of claim 1,
   wherein the reagent and the blood sample react with each other to form the blood sample mixture in the first zone,
   wherein the reaction cassette is configured such that the washing solution is moved from the first zone to the measurement zone by gravity when the reaction cassette is rotated in the first direction without passing through the second zone, after having been rotated in the second direction, so that the washing solution washes the non-glycated hemoglobin from the mixture in the measurement zone.

16. A method for measuring an amount of glycated hemoglobin in a blood sample using a reaction cassette for a glycated hemoglobin meter of claim 1, the method comprising:
   recognizing information for the reaction cassette;
   determining whether the blood sample, the reagent, and the washing solution are discharged into the reaction cassette;
   reacting the blood sample with the reagent to form a first blood sample mixture;
   rotating the reaction cassette to measure the amount of total hemoglobin in the first blood sample mixture;
   rotating the reaction cassette to measure the amount of glycated hemoglobin in a second blood sample mixture, the second blood sample mixture including the first blood sample mixture and washing solution; and
   calculating a ratio of the amount of glycated hemoglobin in the second blood sample mixture with respect to the amount of total hemoglobin in the first blood sample mixture, on the basis of the amount of total hemoglobin and the amount of glycated hemoglobin.

17. The method of claim 16, wherein the determining of whether the blood sample, the reagent, and the washing solution are discharged into the reaction cassette comprises storing the reagent and the washing solution separately in the reaction cassette when a reagent pack is inserted into an upper portion of the reaction cassette.

18. The method of claim 16, wherein the reacting of the blood sample with the reagent comprises shaking the reaction cassette to facilitate reaction of the blood sample with first reagent.

19. The method of claim 16, wherein the rotating of the reaction cassette to measure the amount of total hemoglobin in the first blood sample mixture comprises:

rotating the reaction cassette to move the first blood sample mixture to the measurement zone; and measuring the amount of total hemoglobin in the first blood sample mixture.

20. The method of claim 19, wherein the measuring of the amount of total hemoglobin comprises measuring the amount of total hemoglobin in the first blood sample mixture by an optical reflectometry technique using an optical sensor.

21. The method of claim 16, wherein the rotating of the reaction cassette to measure the amount of glycated hemoglobin in the second blood sample mixture, comprises:

rotating the reaction cassette to move the washing solution to the first zone;

rotating the reaction cassette to move the washing solution in the first zone to the measurement zone; and washing the first blood sample mixture using the washing solution, removing from the first blood sample mixture non-glycated hemoglobin which is not combined with the reagent, to form the second blood sample mixture, and measuring the amount of glycated hemoglobin in the second blood sample mixture.

22. The method of claim 21, wherein, in the rotating of the reaction cassette to move the washing solution to the first zone, when the reaction cassette is rotated, the first blood sample mixture is not moved to the first zone.

23. The method of claim 21, wherein the measuring of the amount of glycated hemoglobin comprises measuring the amount of glycated hemoglobin in the second blood sample mixture by an optical reflectometry technique using an optical sensor.

24. The method of claim 16, wherein the reaction includes a chemical reaction, agitating, and washing.

\* \* \* \* \*